(12) United States Patent
Weidmann

(10) Patent No.: US 6,918,697 B2
(45) Date of Patent: Jul. 19, 2005

(54) LIGHT TREATMENT DEVICE AND METHOD, IMAGING CASSETTE, DOSE MEASURING MODULE AND RADIOLOGY APPARATUS

(75) Inventor: Uwe Weidmann, Buc (FR)

(73) Assignee: GE Medical System Global Technology Company, LLC, Waukesha, WI (US)

(*) Notice: Subject to any disclaimer, the term of this patent is extended or adjusted under 35 U.S.C. 154(b) by 0 days.

(21) Appl. No.: 09/826,202

(22) Filed: Apr. 4, 2001

(65) Prior Publication Data

US 2001/0038078 A1 Nov. 8, 2001

(30) Foreign Application Priority Data

Apr. 6, 2000 (FR) .............................. 00 04407

(51) Int. Cl.⁷ .............................. G03B 42/04
(52) U.S. Cl. .................... 378/185; 250/370.11
(58) Field of Search ................ 378/182–188; 250/370.11, 487.1

(56) References Cited

U.S. PATENT DOCUMENTS 4,139,798 A  2/1979  Hoover ........................ 315/10
5,734,693 A  * 3/1998  Quint et al. ................. 378/185
6,242,114 B1 * 6/2001  Yamasaki et al. ........... 428/690

FOREIGN PATENT DOCUMENTS

| EP | 257728  | 3/1988 |
| EP | 674169  | 9/1995 |
| EP | 857983  | 8/1998 |
| FR | 2753811 | 3/1995 |

OTHER PUBLICATIONS

Patent Abstracts of Japan, Publication No 11160818. Publication Date Jun. 18, 1999.

* cited by examiner

Primary Examiner—Craig E. Church
(74) Attorney, Agent, or Firm—Cantor Colburn LLP

(57) ABSTRACT

Device and method of treatment of light obtained from X-rays, comprising a means of filtering the light with a cutoff frequency such that a first part of the spectrum of the light emitted by a light emitter is preserved, the first part of the spectrum being independent of temperature, and a second part of the light spectrum is stopped, the second part of the spectrum presenting a shift dependent on temperature. The invention also concerns an imaging cassette, a dose measuring module and a radiology apparatus.

60 Claims, 4 Drawing Sheets

LIGHT TREATMENT DEVICE AND METHOD, IMAGING CASSETTE, DOSE MEASURING MODULE AND RADIOLOGY APPARATUS

CROSS-REFERENCE TO RELATED APPLICATIONS

This application claims the benefit of a priority under 35 USC 119 to French Patent Application No. 0004407 filed Apr. 6, 2000, the entire subject matter of which is hereby incorporated by reference.

BACKGROUND OF THE INVENTION

This invention concerns the treatment of light, in general.

This invention can be applied in the field of radiology, in which X-ray detection passes through a stage of transformation of X-rays into light that is visible or close to the visible range.

Patent FR-A-2,753,811 describes a removable digital imaging device to be inserted in a radiology apparatus comprising an X-ray source, a means of maintaining an X-rayed organ and a removable imaging device.

A mammography apparatus contains an X-ray source, placed on one side of the organ to be X-rayed, a support table transparent to X-rays, placed on the other side of the organ to be X-rayed, an adjustable holding plate that applies the organ on the support table and a housing for receiving an imaging cassette containing a printable film or a digital imaging means.

A digital imaging cassette comprises a case in which a radiographic signal detection device is placed inside. The device can contain a scintillator capable of transforming X-radiation into luminous radiation, an optical fiber to filter most of the X-radiation having crossed the scintillator and protecting the components situated after the optical fibers, and a matrix camera with charge transfer elements (CCD) forming a sensitive zone.

However, the images furnished by that type of device are not always of a quality as high as the users might desire.

BRIEF DESCRIPTION OF THE INVENTION

The invention therefore proposes a light treatment device capable of improving the quality of images obtained from an output.

A light treatment device, according to one aspect of the invention, comprises a means of filtering the light, so that a first part of the spectrum of the light emitted by a light emitter is preserved, the first part of the spectrum being independent of temperature, and so that a second part of the light spectrum is stopped, the second part of the spectrum presenting a shift dependent on temperature.

The invention also concerns a radiological imaging cassette containing a light treatment device.

The invention also concerns a dose measuring module containing a light treatment device.

The invention also concerns a radiology apparatus containing a radiological imaging cassette equipped with a light treatment device and/or a dose measuring module provided with a light treatment device.

The invention also concerns a method of treatment of light, in which the light is filtered with a cutoff frequency such that a first part of the spectrum of the light emitted by a light emitter is preserved and a second part of the light spectrum is stopped, the first part of the spectrum being independent of temperature and the second part of the spectrum presenting a shift dependent on temperature.

DETAILED DESCRIPTION OF THE INVENTION

It was realized that the temperature of an imaging means capable of transforming the incident radiation of a first wavelength into a radiation of a different wavelength, in the order of that of visible light, for example, could have an undesirable effect on the quality of the image.

In the case of a dosimeter intended to measure the radiation dose received in a radiology machine and containing an intensifier making it possible to increase the number of photons, while modifying their wavelength, and a photomultiplier making it possible to transform the photons received from the intensifier into electrons for forming an electric signal, it was realized that the characteristics of the intensifier were very sensitive to temperature, notably, the ratio between the number of photons emitted on output and the number of incident photons received on input.

It was also observed that in a radiological imaging cassette containing an intensifier, the intensifier was very sensitive to the effect of temperature.

Figure 1:
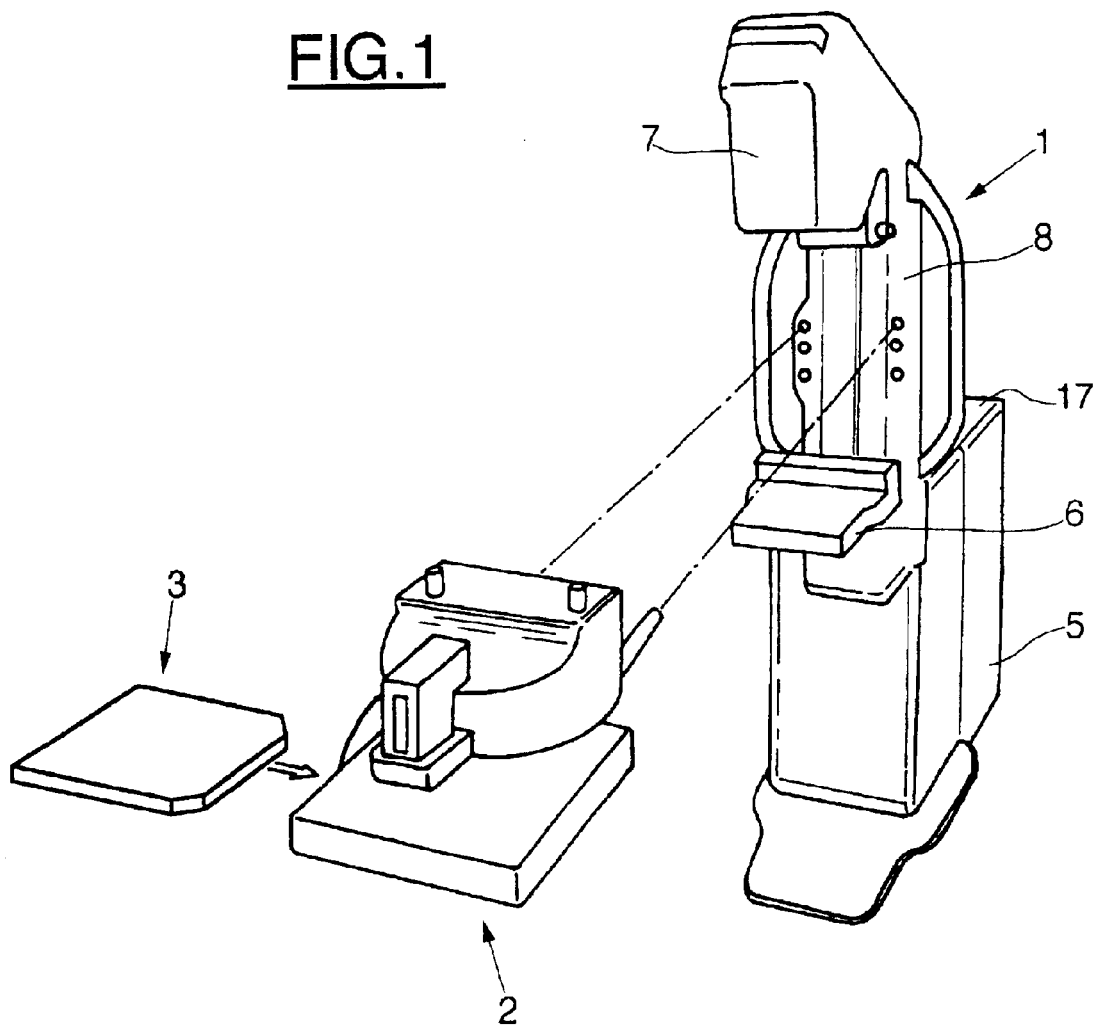
FIG. 1 is a general view in perspective of a radiology apparatus.

As illustrated on FIG. 1, a radiology system comprises a radiology apparatus 1, a puncture system 2, a digital or analog imaging cassette 3 and a control and treatment means. The radiology apparatus 1 comprises a base 5 resting on the floor and supporting a breast-holding plate 6 and an X-ray source 7 which can be tilted in relation to the vertical plane of symmetry of the radiology apparatus 1. The X-ray source 7 is supported by a column 8.

The cassette 3 can be inserted by following the direction of the arrow of FIG. 1 into a housing of the puncture system 2 or into the housing provided in a cassette holder, not represented, used on diagnostic examinations and intended to be fastened on the breast-holding plate 6.

Figure 2:
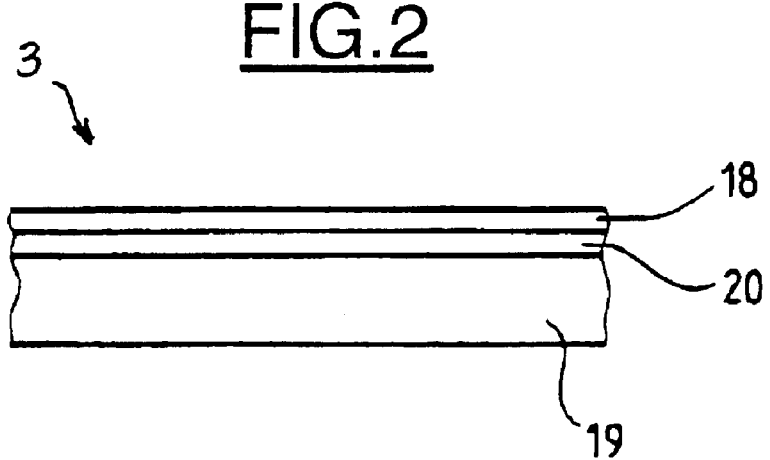
FIG. 2 is a schematic view in cross section of the sensitive zone of an imaging cassette.

As partially illustrated on FIG. 2, a cassette 3 contains an upper wall 18 transparent to X-rays, an intensifier 19 capable of transforming the X-rays into visible light and a detection element 20, for example, a matrix camera composed of a plurality of charge transfer cells called CCD or a photosensitive film.

In operation, the X-rays are emitted by the source 7 (FIG. 1), crossing the holding plate of the puncture system 2, the organ X-rayed, the cassette holder and the upper wall 18 of the cassette 3, and pass into the intensifier 19 which, on reception of X-rays, emits the visible light transferred to the detection element 20. A matrix camera can make possible the transformation of information received in the form of visible light into information in the form of a digital electric signal transmitted by the electric cable 13 to the control and treatment means 4.

In case the detection element 20 is a photosensitive film, no cable is generally provided between the cassette 3 and the treatment means, the cassette is then removed from the housing of the apparatus 1 or from the puncture system 2 for visualization of the image.

As can be seen, in particular, in FIG. 2, the detection element 20 is placed between the upper wall 18 and the intensifier 19 and receives the light emitted by the intensifier 19 on reception of X photons. For example, the intensifier 19 can be made with gadolinium oxysulfite terbium base with a principal light emission peak centered at around 545 nm wavelength. In the case of a photosensitive film, a film presenting a good sensitivity at around 545 nm wavelength may be used. More generally, it is advisable to use an intensifier and a film which are suitably paired. The film, marketed by KODAK under the name "Min-R 2000", could be suitable.

In order to avoid the temperature shift encountered on such cassettes, means for filtering is incorporate in the intensifier 19 in the form of mineral pigments. Either organic or mineral pigments can be provided. Those pigments will be such that the photons of wavelengths close to or higher than those of the principal peak of the intensifier 19 are presented and the photons of lower wavelengths are intercepted by the filtering means.

It was observed that the shift of the ratio between output and input of the intensifier 19, due to temperature, predominantly affected short wavelengths. By filtering the photons of short wavelengths, particularly below 500 nm, and even 400 nm, it is possible to decorrelate the output/input transmission ratio of the intensifier 19 of temperature. That filtering is all the greater as the film is generally sensitive to those short wavelengths.

Figure 3:
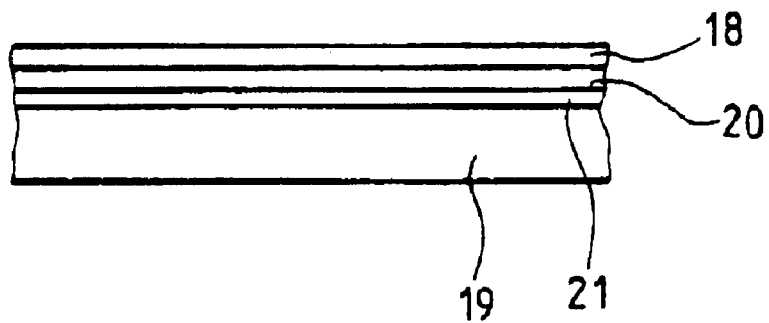
FIG. 3 is another schematic view in cross section of the sensitive zone of an imaging cassette.

In FIG. 3 an embodiment of the invention is illustrated, in which means for the filtering the form of a thin layer 21 arranged between the detection element 20 and the intensifier 19. The thin layer 21 can be made with a base of glass, polycarbonate or even acetate loaded with dyes or pigments to filter the part of the light not desired. The means for filtering can also come in the form of a plurality of thin layers for interference filtering.

Figure 4:
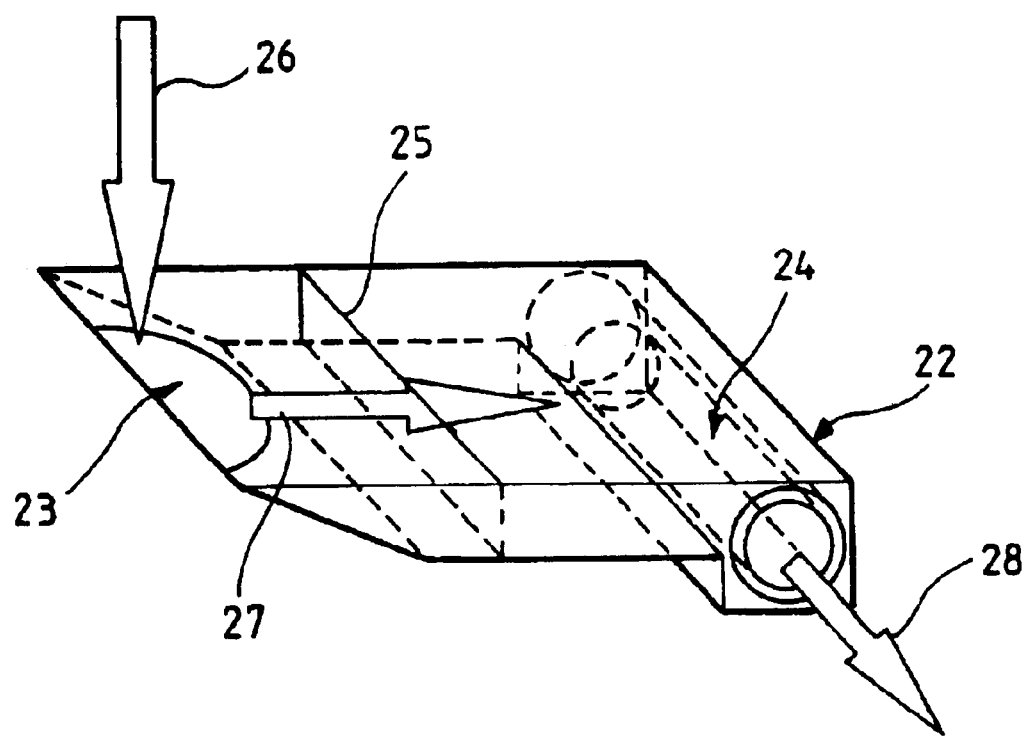
FIG. 4 is a schematic top view in elevation of a dose measuring module.

In FIG. 4 a radiological dose measuring module is illustrated, containing a frame 22 supporting an intensifier 23, a photomultiplier tube 24 and a filter 25. The incident rays, X-rays, for example, arrive in the direction indicated by arrow 26, and are transformed by the intensifier 23 into visible, infrared or ultraviolet light. The light beam emanating from the intensifier 23 is oriented in the direction of arrow 27, crosses the filter 25 and reaches the photomultiplier tube 24, which transforms the photons of the light into electrons generating an electric signal that is emitted by the output represented by arrow 28. The frame 22 forms a guide for the light beam emanating from the intensifier 23.

In other words, it can be arranged for the walls of the frame 22 to be transparent to the incident radiation arriving on the intensifier 23 and to be opaque to the light beam emitted by the intensifier 23. The filter 25 is mounted, for example, by gluing, soldering, clamping or any other suitable type of connection on the optical path of the light beam between the intensifier 23 and the photomultiplier tube 24. The filter 25 will present a suitable cutoff frequency, generally in the range of visible light, that is, between 400 nm and 800 nm. In particular, a cutoff frequency between 450 nm and 600 nm may be provided and preferably between 480 nm and 540 nm, especially between 500 nm and 530 nm. For example, the filter marketed by GENTEX under the name "Filtron E 520" may be suitable. The intensifier 23 may be made of synthetic material.

Figure 5:
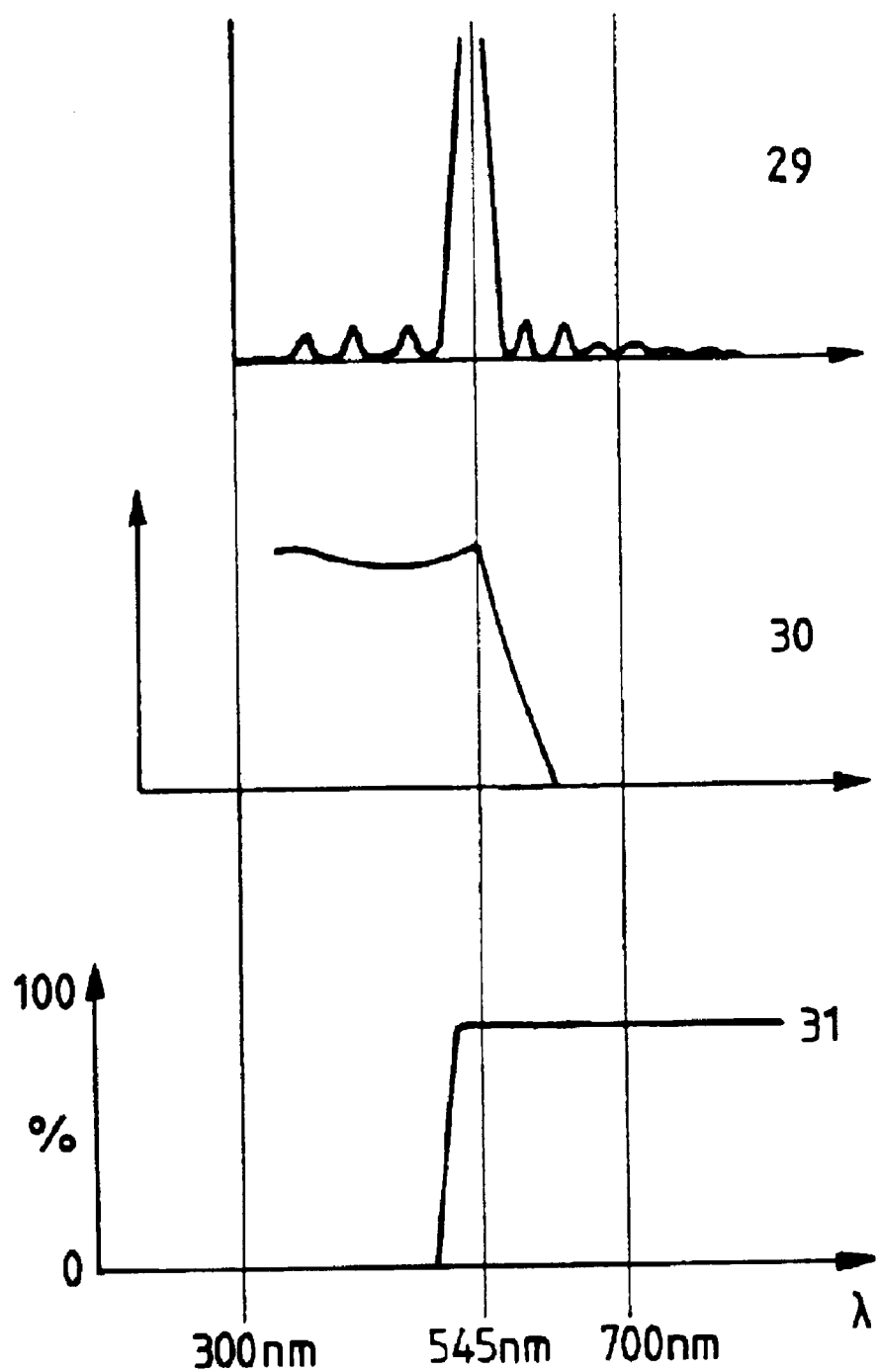
FIG. 5 is a curve showing the sensitivity of an X-ray film as a function of wavelength.

In FIG. 5 three curves are illustrated with the wavelength in abscissa. Curve 29 schematically represents the emission spectrum of an intensifier. Curve 30 represents the sensitivity of a photosensitive film. Curve 31 shows the evolution of transmission of an optical fiber. It is to be noted that the intensifier does not emit photons of wavelengths close to 300 nm and an extremely low quantity of photons of 700 nm wavelength, which will not print film whose sensitivity at around 700 nm is nil. On the other hand, it is to be noted that, in this example, the intensifier presents a principal emission peak centered on 545 nm with secondary peaks for lower wavelengths as well as for higher wavelengths. The sensitivity of the film is good for a wavelength close to 545 nm as well as for lower wavelengths to approximately 300 nm. Sensitivity decreases and becomes nil between 600 and 650 nm.

It has been observed that the temperature shift of the intensifier occurs essentially for the secondary peaks of emissions of wavelengths below the wavelength of the principal peak. A filter is therefore provided, capable of properly transmitting the photons of wavelengths close to those of the principal emission peak of the intensifier and of intercepting the photons of wavelengths corresponding to those of the secondary emission peaks of wavelengths lower than those of the principal emission peak. In this example, an extremely low transmission rate is provided, below 480 nm, and even 450 nm.

An embodiment of the invention provides a means of light treatment capable of solving the problems presented by the light intensifiers which receive radiation of a certain wavelength and emit luminous radiation of a different wavelength.

Such means for light treatment are well suited to imaging cassettes, radiological, for example, whether they contain a photosensitive film or a digital light detection means. The means for light treatment is also well suited to modules measuring the radiation dose received.

In a radiology apparatus those modules can be connected to the control means of the X-ray tube in order to regulate or measure the dose received by the film or the patient. The part of the light sensitive to temperature, that is, whose $\lambda$ frequency is such that the number of photons of $\lambda$ frequency is capable of varying as a function of temperature, is simply intercepted before it induces shifts or errors in measurement.

A cutoff frequency can be determined in order to filter the second part of the spectrum.

Thus, the photons of such frequency that their number is little sensitive to temperature are preserved and the photons of such frequency that their number is sensitive to temperature are stopped. The light can be obtained from X-rays. The light intensity shift due to temperature is eliminated or at least markedly diminished.

In one embodiment of the invention, the device is integrated with an intensifier. The intensifier can incorporate mineral or organic pigments.

In another embodiment of the invention, the device contains means for filtering placed below a light intensifier on the path of the light. The means for filtering may come in the form of a thin film or sheet. The filtering element may be made with a base of glass, polycarbonate, acetate, etc., and be loaded with mineral or organic pigments.

In an embodiment of the invention, the means for filtering is mounted in contact with the intensifier.

In an embodiment of the invention, the cassette contains an analog film.

In another embodiment of the invention, the cassette contains a digital light detector.

The module advantageously contains a photomultiplier tube, the device being mounted above the photomultiplier tube.

The module advantageously contains a light intensifier. The module can contain a light guide.

Various modifications in structure and/or steps and/or function may be made by one skilled in the art without departing from the scope of the invention.

What is claimed is:

1. A method for compensating an emission spectrum comprising:

providing a source of light having an emission spectrum, the source responsive to incident radiation, the source having a first part of the emission spectrum that is independent of the temperature of the source and a second part of the emission spectrum that is dependent on the temperature of the source;

providing a detector that is sensitive to the emission spectrum;

providing a filter between the source and the detector, the filter having a cutoff frequency such that the first part of the emission spectrum is transmitted and the second part of the emission spectrum is intercepted.

2. A device for compensating an emission spectrum comprising:

means for emission of light having a spectrum, the means for emission responsive to incident radiation, the means for emission having a first part of the emission spectrum that is independent of the temperature of the means for emission and a second part of the emission spectrum that is dependent on the temperature of the means for emission;

means for detecting which is sensitive to the emission spectrum; and means for filtering the light disposed intermediate the means for emission and the means for detecting, the means for filtering transmitting the first part of the light spectrum and the second part of the light spectrum is intercepted.

3. The device according to claim 2 wherein the device is integrated with an intensifier.

4. The device according to claim 2 wherein the means for filtering is disposed below a light intensifier on a radiation path.

5. The device according to claim 4 wherein the means for filtering is mounted in contact with the intensifier.

6. The device according to claim 3 wherein the means for filtering is one or more layers of a material to filter the part of the radiation that is intercepted.

7. The device according to claim 4 wherein the means for filtering is mounted in contact with the intensifier.

8. A radiological imaging cassette comprising:

means for emission of light having an emission spectrum, the means for emission responsive to incident radiation, the means for emission having a first part of the emission spectrum that is independent of the temperature of the means for emission and a second part of the emission spectrum that is dependent on the temperature of the means for emission;

means for detecting which is sensitive to the emission spectrum; and means for filtering the light disposed intermediate the means for emission and the means for detecting, the means for filtering permitting the first part of the spectrum of the light emitted to be transmitted and the second part of the light spectrum to be intercepted.

9. The cassette according to claim 8 wherein the cassette is integrated with an intensifier.

10. The cassette according to claim 8 wherein the cassette contains means for filtering disposed below a light intensifier on a radiation path.

11. The cassette according to claim 10 wherein the means for filtering is mounted in contact with the intensifier.

12. The cassette according to claim 8 wherein the cassette contains an analog film.

13. The cassette according to claim 8 wherein the cassette contains a digital light detector.

14. A measuring module containing a device comprising:

means for emission of light having an emission spectrum, the means for emission responsive to incident radiation, the means for emission having a first part of the emission spectrum that is independent of the temperature of the means for emission and a second part of the emission spectrum that is dependent on the temperature of the means for emission;

means for detecting which is sensitive to the emission spectrum; and means for filtering the light disposed intermediate the means for emission and the means for detecting, the means for filtering transmitting the first part of the light spectrum, and the second part of the light spectrum is intercepted.

15. The module according to claim 14 wherein the module is integrated with an intensifier.

16. The module according to claim 14 wherein the module contains means for filtering disposed below a light intensifier on a light path.

17. The module according to claim 16 wherein the means for filtering is mounted in contact with the intensifier.

18. The module according to claim 14 wherein the module contains a photomultiplier tube, the device being mounted above the photomultiplier tube.

19. The module according to claim 14 wherein the module contains a light intensifier.

20. The module according to claim 18 wherein the module contains a light intensifier.

21. The module according to claim 14 comprising means for guiding the light emanating from the means for emission.

22. A radiology apparatus comprising:

means for emission of light having an emission spectrum, the means for emission responsive to incident radiation, the means for emission having a first part of the emission spectrum that is independent of the temperature of the means for emission and a second part of the emission spectrum that is dependent on the temperature of the means for emission;

means for detecting which is sensitive to the emission spectrum; and means for filtering the light disposed intermediate the means for emission and the means for detecting, wherein the first part of the spectrum of the light emitted is transmitted and the second part of the light spectrum is intercepted.

23. The radiology apparatus according to claim 22 wherein the means for detecting contains an analog film.

24. The radiology apparatus according to claim 22 wherein the means for detecting contains a digital radiation detector.

25. A radiology apparatus comprising:
  means for emission of light having an emission spectrum, the means for emission responsive to incident radiation, the means for emission having a first part of the emission spectrum that is independent of the temperature of the means for emission and a second part of the emission spectrum that is dependent on the temperature of the means for emission;
  means for detecting which is sensitive to the emission spectrum; and
  a module containing a device comprising means for filtering the light disposed intermediate the means for emission and the means for detecting, wherein the first part of the spectrum of the light emitted is intercepted and the second part of the spectrum is intercepted.

26. The radiology apparatus according to claim 25 wherein the device is integrated with an intensifier.

27. The radiology apparatus according to claim 25 wherein the device containing the means for filtering is disposed below a radiation intensifier on a radiation path.

28. The radiology apparatus according to claim 25 wherein the device containing the means for filtering is mounted in contact with the intensifier.

29. A method for radiation output comprising:
  providing an intensifier having a light spectrum in response to incident radiation;
  providing a detector, which has a sensitivity to the emission spectrum;
  determining a wavelength of the emission spectrum that is independent of the temperature of the intensifier and another wavelength of the emission spectrum that is dependent of temperature of the intensifier;
  providing a filter between the intensifier and the detector, the filter having a transmission spectrum that suppresses the wavelength that is dependent of the temperature of the intensifier.

30. An article of manufacture comprising:
  means for intensifying having light spectrum in response to incident radiation, the emission spectrum having a wavelength that is temperature sensitive;
  means for detecting that has a sensitivity to the emission spectrum; and
  means for filtering having a transmission spectrum that suppresses the wavelength that the means for intensifying is temperature sensitive.

31. The article according to claim 30 wherein the emission spectrum of the means for intensifying has a selected wavelength that is suppressed by the means for filtering.

32. The article according to claim 30 wherein the emission spectrum of the means for intensifying has a principle peak centered at around 545 nm.

33. The article according to claim 30 wherein the means for filtering and the means for intensifying are integrated.

34. The article according to claim 30 wherein the means for filtering suppresses the wavelength shorter than a principle peak of the emission spectrum of the means for intensifying.

35. The article according to claim 30 wherein the means for filtering comprises material from the group consisting essentially of glass, polycarbonate or acetate, the material having a dye or organic or mineral pigment incorporated therein.

36. The article according to claim 30 wherein the means for filtering is a plurality of layers.

37. The article according to claim 30 wherein the means for detecting is a film.

38. The article according to claim 30 wherein the means for detecting is a photomultiplier tube.

39. The article according to claim 30 wherein the means for detecting is a charge transfer cell.

40. The article according to claim 30 wherein the means for filtering is adapted to transmits radiation close to a principle peak of the emission spectrum of the means for intensifying and to intercepts radiation of wavelength corresponding to those of a secondary emission peak of a wavelength less than those of the principle emission peak.

41. The article according to claim 30 wherein the means for intensifying comprises a base of gadolinium oxysulfite terbium.

42. An article of manufacture comprising:
  means for intensifying having a light spectrum in response to incident radiation, the means for intensifying having an emission spectrum with a wavelength that is temperature sensitive;
  means for detecting that has a sensitivity to the emission spectrum; and
  means for filtering having a transmission spectrum that suppresses the wavelength that the means for intensifying is temperature sensitive;
  the means for filtering suppressing the wavelength shorter than a principle peak of the emission spectrum of the means for intensifying; and
  the means for filtering being disposed between the means for intensifying and the means for detecting.

43. A radiology apparatus comprising:
  a source of emitted radiation;
  a cassette for receiving the emitted radiation, the cassette comprising:
  means for intensifying having a light spectrum in response to the emitted radiation, the light spectrum having a wavelength at which the means for intensifying is temperature dependent;
  means for detecting that has a sensitivity to the light spectrum; and
  means for filtering having a transmission spectrum that suppresses the wavelength that the means for intensifying is temperature dependent;
  the means for filtering suppressing the wavelength shorter than a principle peak of the light spectrum of the means for intensifying; and
  the means for filtering being disposed between the means for intensifying and the means for detecting.

44. A radiation dose measuring module comprising:
  means for intensifying having a light spectrum in response to incident radiation, the emission spectrum having a wavelength at which the means for intensifying is temperature dependent;
  means for detecting that has a sensitivity to the light spectrum; and
  means for filtering having a transmission spectrum that suppresses the wavelength that the means for intensifying is temperature dependent;
  the means for filtering suppressing the wavelength shorter than a principle peak of the light spectrum of the means for intensifying;
  the means for filtering being disposed between the means for intensifying and the means for detecting; and
  a frame supporting the means for intensifying, the means for detecting and the means for filtering,
  the frame forming a guide for the radiation of the light spectrum of the means for intensifying.

45. A method for radiation output comprising:
providing an intensifier having a light emission spectrum in response to incident radiation;
providing a detector, which has a sensitivity to the emission spectrum;
determining a wavelength of the emission spectrum at which the intensifier is temperature dependent; and
providing a filter between the intensifier and the detector, the filter having a transmission spectrum that suppresses the wavelength that the intensifier is temperature dependent.

46. An article of manufacture comprising:
means for intensifying having a light emission spectrum in response to incident radiation;
means far detecting that has a sensitivity to the emission spectrum; and
means for filtering having a transmission spectrum that suppresses a wavelength of the emission spectrum at which the means for intensifying is temperature dependent.

47. The article according to claim 46 wherein the emission spectrum of the means for intensifying has a selected wavelength that is suppressed by the means for filtering.

48. The article according to claim 46 wherein the emission spectrum of the means for intensifying has a principle peak centered at around 545 nm.

49. The article according to claim 46 wherein the means for filtering and the means for intensifying are integrated.

50. The article according to claim 46 wherein the means for filtering suppresses the wavelength shorter than a principle peak of the emission spectrum of the means for intensifying.

51. The article according to claim 46 wherein the means for filtering comprises material from the group consisting of glass, polycarbonate or acetate, the material having a dye or organic or mineral pigment incorporated therein.

52. The article according to claim 46 wherein the means for filtering is a plurality of layers.

53. The article according to claim 46 wherein the means for detecting is a film.

54. The article according to claim 46 wherein the means for detecting is a photomultiplier tube.

55. The article according to claim 46 wherein the means for detecting is a charge transfer cell.

56. The article according to claim 46 wherein the means for filtering transmits radiation close to a principle peak of the emission spectrum of the means for intensifying and intercepts radiation of wavelength corresponding to those of a secondary emission peak of wavelength less than those of the principle emission peak.

57. The article according to claim 46 wherein the means for intensifying comprises a base of gadolinium oxysulfite terbium.

58. An article of manufacture comprising:
means for intensifying having a light emission spectrum in response to incident radiation, the means for intensifying having a wavelength that is temperature dependent;
means for detecting that has a sensitivity to the emission spectrum; and
means for filtering having a transmission spectrum that suppresses the wavelength of the emission spectrum that the means for intensifying is temperature dependent;
the means for filtering suppressing the wavelength shorter than a principle peak of the emission spectrum of the means for intensifying; and
the means for filtering being disposed between the means for intensifying and the means for detecting.

59. A radiology apparatus comprising:
a source of emitted radiation;
a cassette for receiving the emitted radiation, the cassette comprising:
means for intensifying having a light emission spectrum in response to the emitted radiation, the means for intensifying emitting a wavelength that is temperature sensitive;
means for detecting that has a sensitivity to the emission spectrum; and
means for filtering having a transmission spectrum that suppresses the wavelength of the emission spectrum that the means for intensifying is temperature sensitive;
the means for filtering suppressing the wavelength shorter than a principle peak of the emission spectrum of the means for intensifying; and
the means for filtering being disposed between the means for intensifying and the means for detecting.

60. A radiation dose measuring module comprising:
means for intensifying having a light emission spectrum in response to incident radiation, the means for intensifying emitting a wavelength that is temperature dependent;
means for detecting that has a sensitivity to the emission; and
means for filtering having a transmission spectrum that suppresses the wavelength of the emission spectrum that the means for intensifying is temperature dependent;
the means for filtering suppressing the wavelength shorter than a principle peak of the emission spectrum of the means for intensifying;
the means for filtering being disposed between the means for intensifying and the means for detecting; and
a frame supporting the means for intensifying, the means for detecting and the means for filtering,
the frame forming a guide for the radiation of the emission spectrum of the means for intensifying.

* * * * *

UNITED STATES PATENT AND TRADEMARK OFFICE
CERTIFICATE OF CORRECTION

PATENT NO. : 6,918,697 B2
DATED : July 19, 2005
INVENTOR(S) : Uwe Wiedmann

It is certified that error appears in the above-identified patent and that said Letters Patent is hereby corrected as shown below:

Title page,
Item [75], Inventor, after "Uwe" delete "Weidmann" and insert -- Wiedmann --.
Item [56], References Cited, FOREIGN PATENT DOCUMENTS, after "2753811" delete "3/1995" and insert -- 3/1998 --.

Column 2,
Line 16, delete "FIG. 5 is a curve showing the sensitivity of an X-ray film as a function of wavelength." and insert -- FIG. 5 is three curves showing the emission spectrum of an intensifier; the transmission sensitivity of an X-ray film as a function of wavelength; and the transmission spectrum of a filter. --;
Line 40, after "illustrated" delete "on" and insert -- in --;
Line 62, after "organ" delete "X-rayed" and insert -- subject to the X-rays --;
Line 65, after "can" delete "make possible the transformation of" and insert
-- transform --; and
Line 67, after "digital" delete "electric" and insert -- electrical --.

Column 3,
Line 1, after "by" delete "the" and insert -- an --;
Line 1, after "cable" delete "13"; and
Line 2, after "means" delete "4".

Column 4,
Line 6, before "abscissa" delete "in" and insert -- as the --;
Line 7, after "intensifier" insert -- such as intensifier 19 or 23 --;
Line 8, after "film" insert -- such as detector element 20 or 24 --;
Line 9, after "optical" delete "fiber" and insert -- filter, such as the thin layer 21 or 25 --;
Line 9, after "layer 21 or 25." delete "It is to be noted that the intensifier does not emit photons of wavelength close to 300 nm and an extremely low quantity of photons of 700 nm wavelength, which will not print film whose sensitivity at around 700 nm is nil. On the other hand, it is to be noted that, in this example, the intensifier presents a principal emission peak centered on 545 nm with secondary peaks for lower wavelengths as well as for higher wavelengths. The sensitivity of the film is good for a wavelength close to 545 nm as well as for lower wavelengths to approximately 300 nm. Sensitivity decreases and becomes nil between 600 and 650 nm.";
Line 61, after "intensifier" delete "on" and insert -- in --;
Line 62, after "may" delete "come" and insert -- be --; and
Line 63, after "or" insert -- a metal --.

UNITED STATES PATENT AND TRADEMARK OFFICE
CERTIFICATE OF CORRECTION

PATENT NO.   : 6,918,697 B2
DATED        : July 19, 2005
INVENTOR(S)  : Uwe Wiedmann It is certified that error appears in the above-identified patent and that said Letters Patent is hereby corrected as shown below:

Column 5,
Line 11, after "function" insert -- and equivalents thereof --.

Column 9,
Line 15, after "means" delete "far" and insert -- for --.

Signed and Sealed this

Third Day of January, 2006

JON W. DUDAS
*Director of the United States Patent and Trademark Office*